United States Patent
Hirai

(10) Patent No.: US 6,515,171 B1
(45) Date of Patent: *Feb. 4, 2003

(54) PROCESS FOR SEPARATING AN OXIDATION REACTION PRODUCT AND AN OXIDATION CATALYST

(75) Inventor: Naruhisa Hirai, Himeji (JP)

(73) Assignee: Daicel Chemical Industries, Ltd., Osaka (JP)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 714 days.

(21) Appl. No.: 08/912,229

(22) Filed: Aug. 15, 1997

(30) Foreign Application Priority Data

Aug. 20, 1996 (JP) .............................. 8-218693

(51) Int. Cl.[7] .......................... C07C 27/00; C07C 47/54; C07C 49/67; C07B 33/00
(52) U.S. Cl. ..................... 562/512.4; 562/593; 562/580; 562/600; 562/554
(58) Field of Search .............................. 562/512.4, 593, 562/580, 600, 554

(56) References Cited

U.S. PATENT DOCUMENTS 5,030,739 A    7/1991   Foricher et al. ............ 552/542

FOREIGN PATENT DOCUMENTS

JP            0838909 A    2/1996

OTHER PUBLICATIONS

Y. Ishii et al., J. Org. Chem., 61(14):4520–4526 (1996).
English translation of Ishii et al. JP 08–38909 published Feb. 13, 1996.*

* cited by examiner

Primary Examiner—Laura L. Stockton
(74) Attorney, Agent, or Firm—Birch, Stewart, Kolasch & Birch, LLP

(57) ABSTRACT

An oxidation reaction mixture (e.g. adipic acid, benzoic acid, butenediol) and an oxidation catalyst are efficiently separated from a reaction mixture with the use of an aqueous solvent (e.g. methyl benzoate, benzonitrile) containing at least water (e.g. water) and a non-water-soluble solvent separable from the aqueous solvent, the reaction mixture being obtained by oxidizing a substrate (e.g. a hydrocarbon) in the presence of an imide compound such as N-hydroxyphthalimide shown by the following formula (1) as the oxidation catalyst,

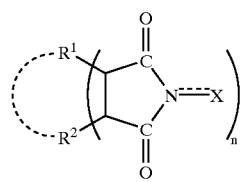

(1)

wherein $R^1$ and $R^2$ represents a substituent such as a hydrogen atom and a halogen atom; $R^1$ and $R^2$ may together form a double bond, or an aromatic or nonaromatic 5- to 12-membered ring; X stands for O or OH; and n is 1 to 3. No decomposition of the oxidation catalyst is observed in this separation process.

20 Claims, No Drawings

PROCESS FOR SEPARATING AN OXIDATION REACTION PRODUCT AND AN OXIDATION CATALYST

FIELD OF THE INVENTION

The present invention relates to a process for separating an oxidation reaction product or its salt, and an oxidation catalyst from a reaction mixture, the reaction mixture being obtained by oxidation of a substrate with using an imide compound such as N-hydroxyphthalimide as the oxidation catalyst.

BACKGROUND OF THE INVENTION

N-hydroxyphthalimide and other imide compounds are known as oxidation catalysts, such oxidation being conducted by allowing a substrate such as a hydrocarbon, an alcohol, an aldehyde, a ketone, an amine and a heterocyclic compound to contact with molecular oxygen (Japanese Patent Application Laid-open No. 38909/1996 (JP-A-8-38909)). An oxidation reaction by means of this catalyst, which can be conducted under mild conditions without any exhaust gas treatment, can provide an oxidation reaction product including an alcohol, an aldehyde, a ketone and an organic acid at a high conversion rate and selectivity. Such an oxidation reaction product is separated from a reaction mixture commonly by distillation.

Distillation, however, is not always an advantageous process for separation of an oxidation reaction product from a reaction mixture. When both of the oxidation reaction product and the substrate have low boiling points (e.g. 50 to 150° C.), distillation results in deterioration of purity and yield owing to the substrate with a low boiling point. On the other hand, when the oxidation reaction product is a compound with a high boiling point (e.g. 150 to 500° C.), the oxidation catalyst might be decomposed during distillation which is carried out at a high temperature with heating. The imide compound has a low decomposition temperature, for example, 230° C. in the case of N-hydroxyphthalimide. Thus, distillation, as a process for separating a high-boiling-point oxidation reaction product, has a risk of thermal decomposition of the oxidation catalyst, failing to reutilise the oxidation catalyst and raising the cost. Besides, the thermally decomposed product of the oxidation catalyst might degrade the quality of the reaction product. As mentioned above, it is not wise to choose distillation for separation of an oxidation reaction product having any boiling point from a reaction mixture without any consideration.

SUMMARY OF THE INVENTION

It is therefore an object of the present invention to provide a process for separating an oxidation catalyst such as N-hydroxyphthalimide or other imide compounds from a reaction mixture obtained by oxidation of a substrate such as a hydrocarbon in order to make effective use of the oxidation catalyst.

It is another object of the present invention to provide a process for efficiently separating the imide compound to be reutilised while preventing decomposition thereof, even when the oxidation reaction product is a compound with a high boiling point.

It is yet another object of the present invention to provide a process for efficient separation of the oxidation reaction product and the oxidation catalyst from the reaction mixture obtained by oxidation of the substrate, the process not being affected by the boiling point of the reaction product.

A further object of the present invention is to provide a process for separating the oxidation reaction product and the oxidation catalyst from the oxidation reaction mixture by an easy operation under mild conditions.

After intensive works for achieving the above objects, the inventor of the present invention has found that, in an oxidation reaction using an imide compound such as N-hydroxyphthalimide as the oxidation catalyst, use of an aqueous solvent at least containing water and a non-water-soluble solvent helps efficient distribution of the oxidation reaction product into an aqueous solvent layer and efficient distribution of the oxidation catalyst into a non-water-soluble solvent layer, each solvent acting as an extracting solvent. The present invention is based on the above findings.

The separation process of the present invention is a process for separating an oxidation reaction product and an oxidation catalyst from a reaction mixture obtained by oxidation of a substrate in the presence of an imide compound shown by the formula (1) as the oxidation catalyst, which process comprises using an aqueous solvent containing at least water and a non-water-soluble solvent separable from the aqueous solvent, thereby efficiently distributing the oxidation reaction product into the aqueous solvent layer and the oxidation catalyst into the non-water-soluble solvent layer,

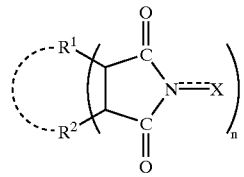

(1)

wherein $R^1$ and $R^2$ independently represents a hydrogen atom, a halogen atom, an alkyl group, an aryl group, a cycloalkyl group, a hydroxyl group, an alkoxy group, a carboxyl group, an alkoxycarbonyl group or an acyl group; $R^1$ and $R^2$ may together form a double bond, or an aromatic or nonaromatic ring; X stands for an oxygen atom or a hydroxyl group; and n denotes an integer of 1 to 3.

The imide compound includes, for instance, N-hydroxyphthalimide and other N-hydroxyimide compounds. As the substrates, there may be mentioned hydrocarbons, alcohols, aldehydes, ketones, amines and heterocyclic compounds. Use of the above substrate provides a corresponding oxidation reaction product (e.g. an alcohol, an aldehyde, a ketone, a carboxylic acid). Water can be used as the aqueous solvent containing at least water (hereinafter it may be referred to as "hydrophilic solvent" or "aqueous solvent"). As the non-water-soluble solvent (hereinafter it may be referred to as "hydrophobic solvent" or "hydrophobic organic solvent"), use can be made of hydrocarbons, ketones, esters and nitriles.

DETAILED DESCRIPTION OF THE INVENTION

[Imide Compound]

In the compound of the formula (1), the halogen atom as the substituents $R^1$ and $R^2$ includes iodine, bromine, chlorine and fluorine atoms. Examples of the alkyl group include methyl, ethyl, propyl, isopropyl, butyl, isobutyl, sec-butyl, t-butyl, pentyl, hexyl, heptyl, octyl, decyl groups and other straight chain or branched chain alkyl groups each having about 1 to 10 carbon atoms. A preferred alkyl group includes an alkyl group having about 1 to 6 carbon atoms, and, in particular, a lower alkyl group having about 1 to 4 carbon atoms.

The aryl group includes, for example, a phenyl group and a naphthyl group. The cycloalkyl group includes cyclopentyl, cyclohexyl, and cyclooctyl groups. As the alkoxy groups, there may be mentioned, for instance, methoxy, ethoxy, propoxy, isopropoxy, butoxy, isobutoxy, t-butoxy, pentyloxy, hexyloxy and other alkoxy groups each having about 1 to 10 carbon atoms. Among them, alkoxy groups each having about 1 to 6 carbon atoms, in especial, lower alkoxy groups each having about 1 to 4 carbon atoms are desirable.

Examples of the alkoxycarbonyl group include methoxycarbonyl, ethoxycarbonyl, propoxycarbonyl, isopropoxycarbonyl, butoxycarbonyl, isobutoxycarbonyl, t-butoxycarbonyl, pentyloxycarbonyl, hexyloxycarbonyl and other alkoxycarbonyl groups each having about 1 to 10 carbon atoms in the alkoxy moiety. A preferable alkoxycarbonyl group includes an alkoxycarbonyl group having about 1 to 6 carbon atoms, above all, a lower alkoxycarbonyl group having about 1 to 4 carbon atoms.

As examples of the acyl group, there may be mentioned formyl, acetyl, propionyl, butyryl, isobutyryl, valeryl, isovaleryl, pivaloyl and other acyl groups each having about 1 to 6 carbon atoms.

The substituents $R^1$ and $R^2$ may be the same, or be different from each other. Further, $R^1$ and $R^2$ in the formula (1) may bond together to form a double bond, or an aromatic or nonaromatic ring. A preferred aromatic or nonaromatic ring has about 5 to 12 members, in particular about 6 to 10 members. The ring may be a heterocycle or condensed heterocycle, but it may practically be a hydrocarbon ring. Such a ring includes, for example, nonaromatic alicyclic rings (e.g. a cyclohexane ring and other cycloalkane rings, each of which may have a substituent, a cyclohexene ring and other cycloalkene rings, each of which may have a substituent), nonaromatic bridged rings (e.g. 5-norbornene ring and other bridged hydrocarbon rings each of which may have a substituent), and other optionally substituted aromatic rings including a benzene ring and a naphthalene ring. The ring may practically comprise an aromatic ring.

A preferred imide compound includes compounds shown by the following formulas (1a) to (1f);

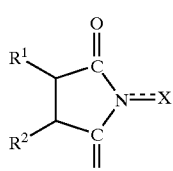

(1a)

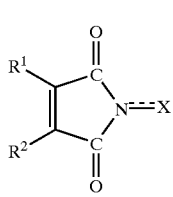

(1b)

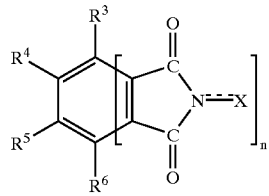

(1c)

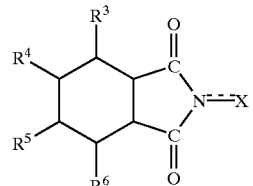

(1d)

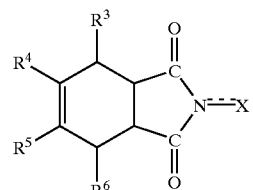

(1e)

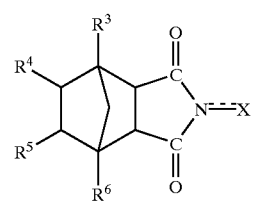

(1f)

wherein $R^3$, $R^4$, $R^5$ and $R^6$ respectively represent a hydrogen atom, an alkyl group, a hydroxyl group, an alkoxy group, a carboxyl group, an alkoxycarbonyl group, an acyl group, a nitro group, a cyano group, an amino group or a halogen atom; and $R^1$, $R^2$, and n have the same meanings as defined above.

In the substituents $R^3$, $R^4$, $R^5$ and $R^6$, the alkyl group includes the same alkyl groups as exemplified above, in particular alkyl groups each having about 1 to 6 carbon atoms. Examples of the alkoxy group include alkoxy groups as mentioned above, among which lower alkoxy groups each having about 1 to 4 carbon atoms are desirable. As examples of the alkoxycarbonyl group, there may be mentioned those as exemplified above, in particular lower alkoxycarbonyl groups each having about 1 to 4 carbon atoms in the alkoxy moiety. The acyl group includes the above-mentioned acyl groups, especially, acyl groups each having about 1 to 6 carbon atoms. The halogen atom includes fluorine, chlorine and bromine atoms, typically speaking. The substituents $R^3$, $R^4$, $R^5$ and $R^6$ may practically be a hydrogen atom, a lower alkyl group having about 1 to 4 carbon atoms, a carboxyl group, a nitro group or a halogen atom.

In the formula (1), X denotes an oxygen atom or a hydroxyl group, and n usually denotes about 1 to 3, preferably 1 or 2. The compounds of the formula (1) may be employed singly or in combination in the oxidation reaction.

As acid anhydrides corresponding to the imide compound of the formula (1), there may be mentioned, for example, succinic anhydride, maleic anhydride and other saturated or unsaturated aliphatic dicarboxylic anhydrides, tetrahydrophthalic anhydride, hexahydrophthalic anhydride (1,2-cyclohexanedicarboxylic anhydride), 1,2,3,4- cyclohexanetetracarboxylic acid 1,2-anhydride and other saturated or unsaturated nonaromatic cyclic polycarboxylic anhydrides (alicyclic polycarboxylic anhydrides), hetic anhydride, himic anhydride and other bridged cyclic polycarboxylic anhydrides (alicyclic polycarboxylic anhydrides), phthalic anhydride, tetrabromophthalic anhydride, tetrachlorophthalic anhydride, nitrophthalic anhydride, trimellitic anhydride, methylcyclohexenetricarboxylic anhydride, pyromellitic anhydride, mellitic anhydride, 1,8;4,5-naphthalenetetracarboxylic dianhydride and other aromatic polycarboxylic anhydrides.

Desirable imide compounds include an imide compound derived from an aliphatic polycarboxylic anhydride (e.g. N-hydroxysuccinimide, N-hydroxymaleimide), an alicyclic polycarboxylic anhydride or an aromatic polycarboxylic anhydride (e.g. N-hydroxyhexahydrophthalimide, N,N'-dihydroxycyclohexanetetra-carboximide, N-hydroxyphthalimide, N-hydroxytetrabromophthalimide, N-hydroxytetrachlorophthalimide, N-hydroxyhetimide, N-hydroxyhimimide, N-hydroxytrimellitimide, N,N'-dihydroxypyromellitimide, N,N'-dihydroxynaphthalenetetracarboximide) and so on. These imide compounds show good oxidizing activities. In respect of separation of the oxidation reaction product and the oxidation catalyst, a preferable imide compound is an imide compound which has high compatibility with and solubility in the hydrophobic solvent, for instance, an imide compound derived from an alicyclic polycarboxylic anhydride or an aromatic polycarboxylic anhydride. It is particularly desirable to make use of an N-hydroxyimide compound derived from an alicyclic polycarboxylic anhydride, above all, from an aromatic polycarboxylic anhydride, such as N-hydroxyphthalimide.

The imide compound is prepared by a conventional imidation process (a process for forming an imide), for instance, by a process which comprises opening the ring of an acid anhydride group by allowing a corresponding acid anhydride to react with hydroxylamine $NH_2OH$, and closing the ring for imidation.

[Co-catalyst]

The oxidation catalyst need not necessarily comprise the imide compound of the formula (1) alone, but may comprise the imide compound of the formula (1) and a co-catalyst. The co-catalyst can be constituted with a transition metal compound (e.g. an oxide, an organic acid salt, an inorganic acid salt, a halide, a complex, a heteropoly acid or its salt), or a boron compound.

The co-oxidizing agent (co-oxidant) used as the co-catalyst includes metal compounds such as a transition metal compound, and a boron compound or other compounds containing a Group 13 element of the Periodic Table of the Elements (e.g. boron B, aluminium Al). The co-oxidizing agent can be used singly or in combination.

As the elements of the transition metal, there may be mentioned, for instance, Group 3 elements of the Periodic Table of Elements (e.g. scandium Sc, yttrium Y, lanthanoid elements such as cerium Ce and samarium Sm, actinoid elements such as actinium Ac), Group 4 elements (e.g. titanium Ti, zirconium Zr), Group 5 elements (e.g. vanadium V, niobium Nb), Group 6 elements (e.g. chromium Cr, molybdenum Mo, tungsten W), Group 7 elements (e.g. manganese Mn, technetium Tc, rhenium Re), Group 8 elements (e.g. iron Fe, ruthenium Ru), Group 9 elements (e.g. cobalt Co, rhodium Rh), Group 10 elements (e.g. nickel Ni, palladium Pd, platinum Pt) and Group 11 elements (e.g. copper Cu). Favourable elements include Ce, V, Nb, Cr, Mo, W, Mn, Fe, Ru, Co, Rh, Ni and Cu.

The species of the co-catalyst is not particularly limited as far as it contains the above element and has oxidizing activities. Although the co-catalyst may be a simple substance of a metal or a hydroxide, it may practically be a metal oxide, a double oxide, oxygen acid or its salt, each containing the above element, an organic acid salt, an inorganic acid salt, a halide, and a coordinate compound (a complex), a heteropolyacid or its salt, each of which contains the metal element.

Examples of the boron compound are a boron hydride, a boric acid, a boric acid salt, a boron oxide, a nitrogen compound, a halide, and a boric acid ester. Preferred boron compounds include a boron hydride, orthoboric acid, and other boric acids or their salts, among which a boric acid is particularly preferable. These co-oxidizing agent can be used alone or as a mixture of two or more.

[Substrate]

By allowing a substrate to contact with molecular oxygen in the presence of the oxidation catalyst, a corresponding oxidation reaction product is efficiently produced.

The substrate includes a variety of compounds which have a position to be oxidized. The examples are ethanthiol, phenylmethanethiol and other thiols; diethyl sulfide, methyl propyl sulfide, diphenyl sulfide and other sulfides; formamide, acetamide and other amides, as well as hydrocarbons, alcohols, aldehydes, ketones, amines and heterocyclic compounds. Desirable substrates include hydrocarbons, alcohols, aldehydes and ketones.

The hydrocarbon, which only needs to have a position to be oxidized (an oxidizable position), includes a saturated or unsaturated aliphatic hydrocarbon which may have a substituent, a saturated or unsaturated alicyclic hydrocarbon which may have a substituent, a condensed cyclic hydrocarbon containing a nonaromatic ring such as a completely or partially hydrogenated condensed polycyclic hydrocarbon, a bridged cyclic hydrocarbon containing a tertiary carbon atom (a methine carbon), a methyl group-containing aromatic hydrocarbon and the like.

As the saturated or unsaturated aliphatic hydrocarbons, there may be mentioned a $C_{4-20}$ saturated hydrocarbon including butane, isobutane, pentane, hexane, octane and decane; a $C_{4-20}$ olefin hydrocarbon such as 2-butene and isobutene; a straight-chain or branched-chain aliphatic hydrocarbon such as butadiene (1,3-butadiene), isoprene (2-methyl-1,3-butadiene) and other conjugated dienes (preferably, isobutane and other branched saturated hydrocarbons; isobutene and other branched unsaturated hydrocarbons; butadiene, isoprene and other conjugated dienes). As the saturated or unsaturated alicyclic hydrocarbons, there may be exemplified cycloalkanes (e.g. cyclobutane, cyclopentane, cyclohexane, cycloheptane, cyclooctane, cyclononane, cyclodecane, cycloundecane, cyclododecane, cyclotridecane, cyclotetradecane, cyclooctadecane, cycloicosane, cyclodocosane, cyclotetracosane, cyclotriacontane); cyclic olefins (e.g. cyclopropene, cyclobutene, cyclopentene, cyclohexene, cycloheptene, cyclooctene, cyclononene, cyclodecene); cycloalkadienes (e.g. cyclopentadiene, 1,3-cyclohexadiene, 1,4-cyclohexadiene, 1,3-cycloheptadiene and other cycloheptadienes, 1,5-cyclooctadiene and other cyclooctadienes); cycloalkatrienes (e.g. cyclooctatriene); and cycloalkatetraenes (e.g. cyclooctatetraene). A desirable alicyclic hydrocarbon has a 3- to 30-membered ring, preferably a 3- to 25-membered ring, and more preferably a 3- to 20-membered ring (e.g. a 5- to 20-membered ring, particularly, a 5- to 16-membered ring).

The polycyclic hydrocarbons such as the condensed polycyclic hydrocarbon and the bridged cyclic hydrocarbon include a compound having at least one methylidyne group (i.e. methine carbon-hydrogen bond —CH<) at a bridgehead position and/or a junction site (a junction position of two rings). The condensed polycyclic hydrocarbons containing a nonaromatic ring such as the completely or partially hydrogenated condensed polycyclic hydrocarbon, which may practically be condensed with a 5- to 8-membered ring (particularly, a 5- or 6-membered ring), includes, for instance, acenaphthene, fluorene, tetralin, indene, indane, perhydroanthracene, perhydrophenanthrene, perhydrophenalene, perhydroacenaphthylene, decalin, hexahydroindane and others. Examples of the bridged cyclic hydrocarbon are bicyclic hydrocarbons (e.g. pinane, pinene, bornane, norbornane, norbornene, bicyclo-[3.2.1]octane, bicyclo[4.3.2]undecane), tricyclic hydrocarbons (e.g. adamantane, exotricyclo[5.2.1.0$^{2,6}$]decane, endotricyclo [5.2.1.0$^{2,6}$]decane), tetracyclic hydrocarbons (e.g. tetracyclo[4.4.0.1$^{2,5}$.1$^{7,10}$]dodecane), dimers of dienes such as dicyclohexadiene and dicyclopentadiene, hydrogenated products of these dimers (e.g. dicyclohexane, dicyclopentane) and their derivatives, and terpenes (e.g. monocyclic monoterpenes, dicyclic monoterpenes, monocyclic sesquiterpenes, dicyclic sesquiterpenes, tricyclic sesquiterpenes, diterpenes, triterpenes, tetraterpenes, polyterpenes and their derivatives). Use may be practically made of, as the bridged cyclic hydrocarbon, a di- to tetra-cyclic hydrocarbon having about 7 to 16 carbon atoms (preferably, about 6 to 14 carbon atoms) as the constituent of the ring (e.g. pinane, bornane, norbornane, norbornene, adamantane).

The methyl group-containing aromatic hydrocarbon need only be a compound in which at least one methyl group is substituted to the aromatic ring (e.g. about 1 to 10, preferably about 1 to 8 methyl groups), the aromatic ring being whichever of an aromatic hydrocarbon ring or an aromatic heterocyclic ring. Examples of the methyl group-containing aromatic hydrocarbon are aromatic hydrocarbons substituted with about 1 to 6 methyl groups such as toluene, (o-, m-, p-) xylene, 1,2,3-trimethylbenzene, 1,2,3,4-tetramethylbenzene, 4-t-butyl-1-methylbenzene, 2-methoxy-1-methylbenzene, 1-methylnaphthalene, 2-methylnaphthalene, 1,5-dimethylnaphthalene and 2,5-dimethylnaphthalene; and di- or tri-aryl-C$_{1-3}$ alkanes such as diphenylmethane, triphenylmethane, dibenzyl and stilbene. A preferable methyl group-containing aromatic compound includes a C$_{6-10}$ aromatic hydrocarbon in which about 1 to 4 methyl groups are substituted per molecule.

The above hydrocarbons may be substituted with various substituents, depending on the species of the hydrocarbon. Examples of the substituents are a halogen atom, an alkyl group, an oxo group, a hydroxyl group, an alkoxy group, a hydroxyalkyl group, a carboxyl group, an alkoxycarbonyl group, an acyl group, an amino group, a substituted amino group, a cyano group and a nitro group.

Desirable hydrocarbons are (1) a conjugated diene (e.g. butadiene, isoprene), (2) a compound having a carbon-hydrogen bond at a position adjacent to an unsaturated bond (e.g. a C$_{4-20}$ olefin hydrocarbon such as 2-butene), (3) an alicyclic hydrocarbon (e.g. a 5- to 16-membered cycloalkane such as cyclohexane and methylcyclohexane, a 5- to 16-membered cycloalkene such as cyclohexene), (4) a condensed cyclic compound (e.g. decalin, tetralin) containing a nonaromatic ring (e.g. a cycloalkane ring or a heterocycle), (5) a bridged cyclic hydrocarbon (e.g. adamantane, norbornene) containing a tertiary carbon atom (a methine carbon), (6) a methyl group-containing aromatic hydrocarbon (e.g. a C$_{6-10}$ aromatic hydrocarbon in which about 1 to 4 methyl groups are substituted per molecule, such as toluene and (o-, m-, p-) xylene), and so on.

By the oxidation of the hydrocarbon, a corresponding oxidized product, such as an alcohol, an aldehyde, a ketone or an organic carboxylic acid, is produced. By way of example, oxidation of a conjugated diene provides a corresponding alkenediol. Meanwhile, a product produced by oxidation of butadiene is a butenediol (a cis- or trans-form of 2-butene-1,4-diol or 1-butene-3,4-diol), the position of the hydroxyl group being not specifically restricted.

The saturated alicyclic hydrocarbon is oxidized, according to the degree of oxidation, into a derivative having a hydroxyl group and/or a derivative having a carbonyl group, and which is further oxidized into a dicarboxylic acid. To give an example, oxidation of cyclohexane provides cyclohexanol and/or cyclohexanone, which is further oxidized into adipic acid. Thus, use of at least one compound selected from cycloalkanes, cycloalkanols or cycloalkanones as a substrate can provide a corresponding dicarboxylic acid.

The condensed cyclic hydrocarbon or the bridged cyclic hydrocarbon is oxidized to give a corresponding oxidation product (a ketone, an alcohol, an aldehyde, a carboxylic acid), in particular, a ketone or an alcohol. A bridged alicyclic hydrocarbon having plural tertiary carbon atoms is oxidized to give, in addition to a monoalcohol, a corresponding polyol in which hydroxyl groups are bonded to the plural tertiary carbon atoms, depending on the conditions. For instance, oxidation of adamantane gives an adamantanol and/or an adamantanepolyol (e.g. adamantanediol, adamantanetriol).

Oxidation of the methyl group-containing aromatic hydrocarbon yields a corresponding oxidized product (an alcohol, an aldehyde, a ketone, a carboxylic acid), particularly a carboxyl group-containing aromatic compound. For instance, benzoic acid, phthalic acid, isophthalic acid or terephthalic acid is produced by oxidation of toluene or (o-, m-, p-) xylene.

The alcohol includes alcohol derivatives of the above-mentioned hydrocarbons, such as aliphatic monohydric alcohols, aliphatic polyhydric alcohols, alicyclic monohydric alcohols, alicyclic polyhydric alcohols and aromatic alcohols.

As the aliphatic monohydric alcohols, there may be exemplified C$_{1-20}$ saturated aliphatic alcohols such as methanol, ethanol, 1-propanol, isopropanol, 1-butanol, isobutanol, 1-pentanol, 2-pentanol, neopentanol, 1-hexanol, 1-octanol, 1-decanol, 1-dodecanol, myristyl alcohol and 1-hexadecanol; and unsaturated aliphatic alcohols such as allyl alcohol, crotyl alcohol, propargyl alcohol, citronellol and geraniol. As the aliphatic polyhydric alcohols, there may be mentioned ethylene glycol, propylene glycol, trimethylene glycol, 1,2-butanediol, 1,3-butanediol, 1,4-butanediol, 1,6-hexanediol, 2,5-hexanediol, neopentyl glycol, pinacol, and glycerin. As the alicyclic monohydric alcohols, there may be mentioned alicyclic monohydric alcohols having 5 to 30 ring members, such as cyclopentanol, cyclohexanol, cycloheptanol, cyclooctanol, cyclodecanol, cycloundecanol, cyclododecanol, cyclotetradecanol, cycloicosanol, methylcyclohexanol, cyclohexen-1-ol, cycloocten-1-ol, cyclogeraniol, borneol and menthol. A preferable alicyclic monohydric alcohol includes a compound with 5 to 30 ring members, preferably with 5 to 25 ring members and more preferably with 5 to 20 ring members (e.g. 5 to 16 ring members). The alicyclic polyhydric alcohol includes 1,2-cyclohexanediol and 1,4-cyclohexanediol, to name a few. As the aromatic alcohols, there may be exemplified benzyl alcohol, salicyl alcohol, benzhydrol and phenetyl alcohol.

A primary or secondary alcohol is desirable among these alcohols, which may be any of the aliphatic alcohol, the alicyclic alcohol or the aromatic alcohol.

Desirable alcohols are (1) a compound having a hydroxyl group at a position adjacent to an unsaturated bond (e.g. unsaturated aliphatic alcohols and aromatic alcohols including allyl alcohol, benzyl alcohol, benzhydrol), (2) an alicyclic alcohol (e.g. a $C_{5-16}$ cycloalkanol such as cyclohexanol and methylcyclohexanol), (3) an alicyclic alcohol (e.g. borneol) having a tertiary carbon atom (a methine carbon) and the like.

Oxidation of the alcohol gives a corresponding aldehyde, ketone or carboxylic acid. By way of illustration, the alicyclic alcohol provides, according to the degree of oxidation, a corresponding alicyclic ketone or polycarboxylic acid. Oxidation of 2-methylcyclohexanol yields 2-methylcyclohexanone, and, further, 2-methyladipic acid.

The aldehydes include aldehyde derivatives of the above hydrocarbons. Examples of the aldehydes are aliphatic aldehydes which includes $C_{1-20}$ saturated aliphatic aldehydes such as formaldehyde, acetaldehyde, propionaldehyde, butylaldehyde, hexanal, octaldehyde and nonaldehyde, unsaturated aliphatic aldehydes such as acrolein, geranial and citronellal, and aliphatic polyaldehydes such as glyoxal, malonaldehyde, succinaldehyde, glutaraldehyde, adipaldehyde, pimelaldehyde, suberaldehyde and sebacaldehyde; aromatic aldehydes such as benzaldehyde, oxybenzaldehyde, cinnamaldehyde, salicylaldehyde, anisaldehyde, 1-naphtylaldehyde, vanillin (vanilaldehyde), phthalaldehyde, isophthalaldehyde and terephthalaldehyde; alcyclic aldehydes such as formylcyclohexane; heterocyclic aldehydes such as nicotin-aldehyde and furfural.

Oxidation of the aldehyde gives a corresponding carboxylic acid. For example, oxidation of adipinaldehyde provides adipic acid.

The ketones include ketone derivatives of the aforesaid hydrocarbons, such as aliphatic ketones, alicyclic ketones, aromatic ketones and heterocyclic ketones. As the aliphatic ketones, there may be mentioned $C_{2-20}$ aliphatic ketones such as acetone, methyl ethyl ketone, diethyl ketone, dipropyl ketone, methyl propyl ketone, methyl butyl ketone and pinacolone. The alicyclic ketones include 4- to 30-membered alicyclic ketones (cyclic ketones) such as cyclobutanone, cyclopentanone, cyclohexanone, cyclooctanone, cyclononanone, cyclodecanone, cycloundecanone, cyclododecanone, cyclotetradecanone, cyclooctadecanone, cycloicosanone, 2-methylcyclohexanone, 2-ethylcyclohexanone, 2,6-dimethylcyclohexanone, 4-chlorocyclohexanone, 4-methoxycyclohexanone, cyclohexanedione, cyclopentenone, cyclohexenone, cyclooctenone, cyclodecenone, menthone and camphor. Preferred alicyclic ketones include a compound having 5 to 20 ring members, more preferably 5 to 16 ring members. As the aromatic ketones, there may be mentioned acetophenone, propiophenone, benzophenone, deoxybenzoin and 1-naphthalenone. The heterocyclic ketones include inden-1-one, 1,2,3-indanetrione, fluoren-9-one, 4-pyranone and other heterocyclic ketones.

Oxidation of the ketone gives a corresponding carboxylic acid. To give a few example, oxidation of diethyl ketone provides acetic acid and propionic acid. Oxidation of cyclooctanone yields suberic acid.

A primary or secondary amine is preferable among the amines. Examples of the amines are aliphatic amines such as methylamine, ethylamine, propylamine, butylamine, dimethylamine, diethylamine, dibutylamine, ethylenediamine, 1,4-butanediamine, hydroxylamine and ethanolamine; alicyclic amines such as cyclopentylamine and cyclohexylamine; aromatic amines such as benzylamine and toluidine. Oxidation of the amine provides a corresponding Schiff base and/or oxime.

As the heterocyclic compounds, there may be exemplified (a) a nonaromatic heterocyclic compound or a condensed cyclic hydrocarbon containing a nonaromatic heterocycle (e.g. pyran, pyrazoline, piperidine, piperadine, indoline, isoindoline, chromene, xanthene, chromane, isochromane), and (b) a heterocyclic compound which has an aromatic heterocycle and a methyl or methylene group in a position adjacent to the aromatic heterocycle (e.g. heterocyclic compounds in which an alkyl group having about 1 to 6 carbon atoms is substituted to an aromatic heterocycle containing 1 to 3 hetero atoms selected from an oxygen atom, a sulfur atom or a nitrogen atom, such as 2-methylfuran, 2,5-dimethylfuran, 2-methylthiophene, 2,5-dimethylthiophene, 2-methylpyridine, 3-methylpyridine, 4-methylpyridine, 2,5-dimethylpyridine, 3-ethylpyridine and 2-methylquinoline). These heterocyclic compounds are oxidized to give corresponding alcohols, ketones or carboxylic acids. Oxidation of the heterocyclic compound (a) converts a methylene group in a position adjacent to a hetero atom (e.g. an oxygen atom, a sulfur atom, a nitrogen atom) into a carbonyl group in the nonaromatic heterocycle, and produces a compound having a corresponding carbonyl group. By oxidizing the heterocyclic compound (b), a compound having a methyl group in a position adjacent to the aromatic heterocycle provides a corresponding heterocyclic aldehyde or a corresponding heterocyclic carboxylic acid, and a compound having a methylene group in a position adjacent to the aromatic heterocycle provides a corresponding heterocyclic ketone.

Among the above oxidation reaction products, preferable compounds include a compound having compatibility with or solubility in the aqueous solvent containing water at least, examples of which are an aliphatic or aromatic carboxylic acid having about 1 to 12 carbon atoms (particularly, adipic acid and other aliphatic carboxylic acids; above all, aliphatic polycyclic acids); a heterocyclic carboxylic acid (e.g. picolinic acid); an alcohol having about 1 to 20, preferably about 2 to 15, carbon atoms, especially an aliphatic monohydric alcohol having about 2 to 4 carbon atoms (e.g. t-butanol); and a polyol (e.g. polyols including an alkenediol such as butenediol obtained by oxidation of the above conjugated diene, and a polyol having a bridged ring such as an adamantanepolyol produced by oxidation of the bridged cyclic hydrocarbon having plural tertiary carbon atoms). In addition, carboxylic acids except the above-mentioned carboxylic acid having about 1 to 12 carbon atoms are preferable, including an aromatic carboxylic acid having about 7 to 16 carbon atoms (e.g. benzoic acid), and an aliphatic or alicyclic carboxylic acid having about 13 to 20 carbon atoms.

The boiling point of the oxidation reaction product is not strictly limited, and is, for instance, about 0 to 500° C. Even if the oxidation reaction product has a high boiling point of about 150 to 500° C., the process of the present invention ensures efficient separation of the oxidation reaction product and the imide compound while suppressing decomposition of the imide compound.

The oxidation reaction with the use of the imide compound shown by the formula (1) proceeds smoothly even under comparatively mild conditions. The reaction temperature can be liberally selected according to the species of the imide compound and the substrate, and, for example, is about 0 to 300° C., preferably about 30 to 250° C., and more preferably about 40 to 200° C. The reaction may practically be conducted at around 40 to 150° C. (e.g. 50 to 100° C.). The reaction can be performed either under atmospheric pressure or under elevated pressure, in which case the pressure may practically be about 1 to 100 atm (e.g. 1.5 to 80 atm), preferably about 2 to 70 atm, and more preferably about 5 to 50 atm. The reaction time can be suitably selected from a range of about 30 minutes to 48 hours, preferably about 1 to 36 hours, and more preferably about 2 to 24 hours, considering the reaction temperature and the pressure.

In the present invention, by using both an aqueous solvent containing at least water and a non-water-soluble solvent, an oxidation reaction product and an oxidation catalyst are respectively distributed into a layer of the aqueous solvent and a layer of the non-water-soluble solvent, thereby separating the oxidation reaction product and the oxidation catalyst. In other words, the reaction mixture is treated by shaking or the like, with the use of the aqueous solvent containing at least water and the non-water-soluble solvent separable from the aqueous solvent, whereby the oxidation reaction product is distributed into the aqueous solvent layer and the oxidation catalyst into the non-water-soluble solvent layer, being separated from each other. According to the above extraction method, which does not specially require any high-temperature heating, the oxidation catalyst can be effectively separated in an easy manner under mild conditions without a fear of being decomposed, so that the catalyst can be reused. In addition, even when the oxidation reaction product has a high boiling point, this process ensures efficient separation of the oxidation reaction product and the oxidation catalyst, and the oxidation catalyst is still reusable.

[Aqueous Solution containing at least Water]

As the aqueous solution containing water at least, use can be made of an aqueous solvent comprising water as the principle component. This aqueous solution includes a mixture of water and a water-soluble organic solvent (e.g. $C_{1-3}$ alcohols such as methanol, ketones such as acetone, ethers such as dioxane and tetrahydrofuran). The proportion of the organic solvent in the mixed solvent is about 0 to 25% by weight (generally, 0 to 10% by weight) relative to water. A preferable aqueous solvent is water. Where necessary, an aqueous solution containing a basic substance may be employed for the formation of a salt of a carboxylic acid.

[Non-water-soluble Solvent]

The non-water-soluble solvent need only be separable from the aqueous solvent. Examples of the non-water-soluble solvent include hydrocarbons (e.g. aliphatic hydrocarbons, alicyclic hydrocarbons, aromatic hydrocarbons, halogenated hydrocarbons), alcohols, ketones, esters, nitro compounds, nitrites and mixtures of these solvents. Use can be optionally made among them, according to the species of the oxidation reaction product or the oxidation catalyst. These hydrophobic solvent may be added to the reaction mixture after completion of the oxidation reaction, or may be used as the reaction solvent. If used as the reaction solvent, the hydrophobic solvent can be further used, after the oxidation reaction, as a separation solvent from the aqueous solvent. In the case where a hydrophobic substrate (e.g. a hydrocarbon, a ketone) is used as the substrate and also used as the reaction solvent after the oxidation reaction, the remaining substrate can be utilised as the separation solvent from the aqueous solvent.

Examples of the hydrocarbon include aliphatic hydrocarbons, alicyclic hydrocarbons, aromatic hydrocarbons and halogenated hydrocarbons. As the aliphatic hydrocarbons, there may be mentioned $C_{5-15}$ aliphatic hydrocarbons such as pentane, hexane, isohexane, heptane, isoheptane, octane, isooctane and decane. A preferable aliphatic hydrocarbon includes a $C_{5-12}$ hydrocarbon (particularly, a $C_{6-10}$ hydrocarbon). As the alicyclic hydrocarbons, there may be exemplified $C_{5-15}$ alicyclic hydrocarbons such as cyclopentane, cyclohexane, methylcyclohexane, dimethylcyclohexane, ethylcyclohexane, cycloheptane and cyclooctane. A desirable alicyclic hydrocarbon includes a $C_{5-12}$ alicyclic hydrocarbon. Examples of the aromatic hydrocarbon include $C_{6-12}$ aromatic hydrocarbons such as benzene, toluene, ethylbenzene, cumene and (o-, m-, p-) xylene. As the halogenated hydrocarbons, there may be exemplified chloromethane, dichloromethane, chloroform, carbon tetrachloride, dichlorodifluoromethane (freon), dichloroethane, trichloroethylene, dichloropropane, dichloropentane, chlorobenzene, dichlorobenzene and trichlorobenzene.

The alcohols include alcohol derivatives of the above hydrocarbons, examples of which are aliphatic alcohols, alicyclic alcohols and aromatic alcohols. As the aliphatic alcohols, there may be mentioned aliphatic monohydric alcohols having 4 to 15 carbon atoms including butanol, heptanol, hexanol, methylhexanol, ethylhexanol, heptanol, octanol and decanol. As the alicyclic alcohols, there may be mentioned alicyclic alcohols having 5 to 15 carbon atoms including cyclohexanol, methylcyclohexanol, ethylcyclohexanol, cycloheptanol and cyclooctanol. The aromatic alcohol includes aromatic alcohols having 6 to 12 carbon atoms such as benzyl alcohol and phenethyl alcohol.

The ketones include ketone derivatives of the above-mentioned hydrocarbons such as aliphatic ketones and alicyclic ketones. As the ketones, there may be exemplified aliphatic ketones having 4 to 15 carbon atoms such as methyl ethyl ketone, methyl isobutyl ketone and diisobutyl ketone; and alicyclic ketones having 5 to 15 carbon atoms such as cyclohexanone, methylcyclohexanone, cycloheptanone and cyclooctanone.

As the esters, use can be made of an ester compound having 3 to 20 carbon atoms. Examples of the ester are $C_{2-10}$ carboxylic acid-$C_{1-10}$ alkyl esters including methyl acetate, ethyl acetate, propyl acetate, isopropyl acetate, butyl acetate, hexyl acetate, amyl acetate, isoamyl acetate, 2-ethylhexyl acetate, methyl propionate, ethyl propionate, butyl propionate, hexyl propionate, amyl propionate, ethyl valerate, ethyl hexanoate, ethyl heptanoate, ethyl octanoate, and ethyl decanoate; $C_{2-4}$ carboxylic acid-$C_{5-10}$ cycloalkyl esters such as cyclohexyl acetate and cyclooctyl acetate; aryl esters such as phenyl acetate and phenyl propionate; $C_{7-12}$ aromatic carboxylic acid-$C_{1-10}$ alkyl esters including methyl benzoate, ethyl benzoate, butyl benzoate, dimethyl phthalate, diethyl phthalate and dibutyl phthalate; and other ester compounds.

The nitro compounds include nitro compounds having 2 to 10 carbon atoms, such as aliphatic nitro compounds including nitroethane, nitropropane and nitropentane; and aromatic nitro compounds including nitrobenzene, dinitrobenzene, nitrotoluene and nitroxylene.

The nitrile includes a nitrile having 7 to 12 carbon atoms including benzonitrile and other $C_{7-12}$ aromatic nitrites.

Favourable non-water-soluble solvents include the hydrocarbons, the ketones, the esters and the nitrites. It is more favourable to use a hydrocarbon having 5 to 15 carbon atoms (e.g. hexane, cyclohexane, toluene), a ketone having 4 to 15 carbon atoms (e.g. methyl ethyl ketone, cyclohexanone), an ester compound having 3 to 20 carbon atoms (e.g. ethyl acetate, phenyl acetate, methyl benzoate) and a nitrile having 7 to 12 carbon atoms (e.g. benzonitrile).

The proportion of the hydrophilic solvent to the hydrophobic solvent can be suitably determined according to the species of the oxidation reaction product and the oxidation catalyst. For instance, the former/the latter is in the range of about 0.1/1 to 10/1, preferably about 0.2/1 to 5/1, and more preferably about 0.3/1 to 3/1 (by weight). In general, the proportion is about 0.5/1 to 2/1 (by weight).

The frequency of extraction of the reaction mixture using the hydrophilic solvent and the hydrophobic solvent can be arranged depending on the species of the oxidation reaction product and the oxidation catalyst. The extraction can be conducted about 1 to 5 times, generally about 1 to 3 times.

The extraction step separates the oxidation reaction product and the oxidation catalyst, carrying (transferring) the oxidation reaction product having the hydrophilic group into the aqueous solvent layer and the imide compound as the oxidation catalyst into the hydrophobic solvent layer. The oxidation catalyst may be, together with the extracting solvent, recycled into the reaction system or reutilised. The substrate can be also used effectively, if being non-water-soluble and acting as the reaction solvent as well, because the remaining substrate after the oxidation reaction can be used as the hydrophobic solvent separable from the aqueous solvent. The non-water-soluble substrate includes hydrocarbons (e.g. aliphatic, alicyclic or methyl group-containing aromatic hydrocarbons) and ketones (e.g. aliphatic or alicyclic ketones). Incidentally, a water-soluble substrate is extracted into the aqueous solvent layer with the oxidation reaction product.

The oxidation catalyst, the substrate and the oxidation reaction product, having been extracted by a liquid-separating operation using the aqueous solvent and the hydrophobic organic solvent, are recovered by a conventional separation process such as filtration, concentration, distillation, extraction, crystallisation, recrystallisation, column chromatography or a combination of these processes.

The co-catalyst may be separated by the same process as above, where necessary.

In the case where the oxidation reaction product is an organic carboxylic acid (e.g. aliphatic carboxylic acids such as adipic acid, suberic acid and sebacic acid; aromatic carboxylic acids such as benzoic acid, phthalic acid, isophthalic acid and terephthalic acid; other carboxylic acids), a salt of the organic carboxylic acid can be efficiently led into the aqueous solvent layer, where necessary, by converting the organic carboxylic acid into a corresponding salt with the use of a base. A free organic carboxylic acid can be generated by adding an acid to the extracted carboxylic acid salt. As the base, use can be made of an inorganic base or an organic base. The inorganic base includes, for instance, ammonia; a hydroxide of an alkali metal such as sodium hydroxide and potassium hydroxide; a hydrogencarbonate of an alkali metal such as sodium hydrogencarbonate and potassium hydrogencarbonate; a carbonate of an alkali metal such as sodium carbonate and potassium carbonate; a hydroxide of an alkaline earth metal such as calcium hydroxide; a carbonate of an alkaline earth metal such as calcium carbonate; and the like. The organic base includes an amine (e.g. aliphatic amines such as dimethylamine, diethylamine, trimethylamine, triethylamine, methylenediamine and ethylenediamine; heterocyclic amines such as pyridine and morpholine) and other compounds containing a basic nitrogen atom.

The carboxylic acid can be extracted by addition of the basic substance or by pH control. The pH of the extraction system may range from about 5 to 10, preferably from about 6 to 8.

The amount of the basic substance can be decided in relation to the species of the oxidation reaction product. For example, the amount is not less than about 0.5 equivalent (e.g. 0.7 to 5 equivalents), preferably about 0.8 to 3 equivalents (e.g. about 0.9 to 1.5 equivalent) and more preferably about 0.8 to 1.5 equivalent (e.g. about 0.9 to 1.2 equivalent), relative to 1 equivalent of the carboxylic acid.

It should be noted that too much addition of the basic substance may end in poor separation efficiency of a carboxylic acid and an oxidation catalyst, when the oxidation catalyst is weakly acidic.

As the acid for generating the free organic carboxylic acid from the carboxylic acid salt, use can be made of an inorganic acid (e.g. hydrochloric acid, sulfuric acid, nitric acid, phosphoric acid) or an organic acid (e.g. an organic carboxylic acid such as acetic acid and propionic acid; an organic sulfonic acid such as methanesulfonic acid, ethanesulfonic acid, p-toluenesulfonic acid and benzenesulfonic acid).

Extraction in this invention may be conducted under heating. The extraction temperature is, for example, about 0 to 100° C., preferably about 5 to 50° C., and more preferably about 10 to 35° C., practically being about 15 to 30° C. For an enhanced extraction efficiency, extraction may be conducted, if necessary, under an influence of shearing force, and under atmospheric or elevated pressure.

The process of the present invention, in which the extraction step employs the aqueous solvent containing at least water and the non-water-soluble solvent, enables not only efficient separation of the oxidation reaction product and the oxidation catalyst but also effective reutilisation of the oxidation catalyst and/or the substrate. In terms of cost and safety, this process is of great advantage for separation and purification of the oxidation reaction product on an industrial basis.

According to the process of the present invention, since the oxidation reaction product and the oxidation catalyst are separated from the reaction mixture obtained by oxidation of the substrate in the presence of the oxidation catalyst shown by the formula (1) with the use of the aqueous solvent containing at least water and the non-water-soluble solvent separable from the aqueous solvent, the oxidation catalyst, saved from decomposition, can be efficiently separated and re-utilised. Even if the oxidation reaction product is a compound with a high boiling point, the oxidation catalyst can be efficiently separated for reutilisation without being decomposed. Besides, the process is not affected by the boiling point of the oxidation reaction product, ensuring efficient separation of the oxidation reaction product and the oxidation catalyst. The oxidation reaction product and the oxidation catalyst can be separated in an easy manner under mild conditions with no need for high-temperature heating.

The following examples are intended to describe the present invention in further detail and should by no means be interpreted as defining the scope of the invention.

EXAMPLES

Example 1

Cyclohexane (20 ml) and water (150 ml) were added at 26° C. to a model mixture for an oxidation reaction mixture composed of cyclohexane (2.548 g, 30 mmol), cyclohexanone (1.472 g, 15 mmol), adipic acid (0.731 g, 5 mmol), N-hydroxyphthalimide (0.816 g, 5 mmol) and benzonitrile (150 ml), and mixed completely. The resulting mixture was laid still so as to be separated into two layers. More water was added to the separated organic layer and mixed completely, and the mixture was separated into two layers. The water layers and the organic layer were analysed by gas chromatography and liquid chromatography. The recovery of cyclohexanone in the organic layer was 93%. The extraction rate of N-hydroxyphthalimide in the organic layer was 77%. The extraction rate of adipic acid in the water layer was 98%.

Example 2

Water (140 ml) was added to a model mixture for an oxidation reaction mixture composed of cyclohexane (2.548 g, 30 mmol), cyclohexanone (1.472 g, 15 mmol), adipic acid (0.731 g, 5 mmol), N-hydroxyphthalimide (0.861 g, 5 mmol) and methyl benzoate (140 ml). The mixture was mixed completely at 26° C. and separated into two layers. Water was further added to the separated organic layer, and the mixture was mixed completely, left still and separated into two layers. The water layers and the organic layer were analysed by gas chromatography and liquid chromatography. The recovery of cyclohexanone in the organic layer was 94%. The extraction rate of N-hydroxyphthalimide in the organic layer was 80%. The extraction rate of adipic acid in the water layer was 97%.

Example 3

A mixture of cyclohexane (4.028 g, 50 mmol), N-hydroxyphthalimide (0.816 g, 5 mmol), acetylacetonatocobalt(II) Co(AA)$_2$ (0.015 g, 0.025 mmol) and benzonitrile (200 ml) was made to react for six hours at 100° C. under an oxygen atmosphere. Thus obtained was a reaction mixture containing cyclohexane (2.946 g, 35 mmol), cyclohexanone (0.981 g, 10 mmol), adipic acid (0.731 g, 2 mmol), N-hydroxyphthalimide and benzonitrile.

To this mixture, cyclohexane (20 ml) and water (150 ml) were added at 26° C. and mixed completely. The mixture was laid still to be separated into two layers. The separated organic layer was further fed with water, mixed completely, and separated into layers. The water layers and the organic layer were analysed by gas chromatography and liquid chromatography. The recovery of cyclohexanone into the organic layer was 94%. The extraction rate of N-hydroxyphthalimide in the organic layer was 79% based on the amount of N-hydroxyphthalimide in the reaction mixture. The extraction rate of adipic acid was 99% in the water layer.

Example 4

A mixture of adamantanol (25 g, 164.2 mmol), N-hydroxyphthalimide (5.36 g, 32.8 mmol), acetylacetonatovanadium(III) V(AA)$_3$ (0.114 g, 0.328 mmol), benzonitrile (150 ml) and acetic acid (150 ml) was made to react for 20 hours at 85° C. under an oxygen atmosphere, thereby giving a reaction mixture containing adamantanol (1.41 g, 9.2 mmol), an adamantanediol (13.9 g, 82.6 mmol), an adamantanetriol (10.5 g, 57.5 mmol), N-hydroxyphthalimide, benzonitrile and acetic acid.

After acetic acid was distilled off from the reaction mixture, more benzonitrile was added thereto in order to make the volume 300 ml. Water (300 ml) was added to the mixture and mixed completely. Then the mixture was separated into layers by leaving the mixture still. The separated organic layer was added with additional water, mixed completely and separated into a water layer and an organic layer. Gas chromatography and liquid chromatography for the water layers and the organic layer indicated that, in the organic layer, adamantanol was recovered at 98% and N-hydroxyphthalimide was extracted at 80% based on the amount of N-hydroxyphthalimide in the reaction mixture; and the adamantanediol and the adamantanetriol were extracted into the water layer at the extraction rates of 92% and 99%, respectively.

Example 5

In the presence of an N-hydroxyphthalimide catalyst (1 mmol), isobutane (10 mmol) was oxidized in a benzonitrile solvent (40 ml) for four hours at 90° C. under an oxygen atmosphere to give a reaction mixture containing t-butanol and acetone (conversion rate of isobutane 90%, yield of t-butanol 80%, yield of acetone 5%). The reaction mixture was extracted twice by using 40 ml of water each to obtain a water layer and an organic layer. The thus separated layers were analysed by gas chromatography and liquid chromatography. In the water layer, the extraction rate of t-butanol was 94%, and that of acetone was 100%. In the organic layer, the extraction rate of N-hydroxyphthalimide was 81%, based on the amount of N-hydroxyphthalimide in the reaction mixture. The N-hydroxyphthalimide was recovered by concentrating the organic layer to remove the solvent and unreacted isobutane.

Example 6

In the presence of an N-hydroxyphthalimide catalyst (1 mmol), 1,3-butadiene (10 mmol) was oxidized in a benzonitrile solvent (40 ml) for six hours at 70° C. under an oxygen atmosphere to give a reaction mixture containing 1,4-butenediol (conversion rate of 1,3-butadiene 90%, yield of 1,4-butenediol 72%). The reaction mixture was extracted twice by using 40 ml of water each to obtrain a water layer and an organic layer. The thus separated layers were analysed by gas chromatography and liquid chromatography. The extraction rate of 1,4-butenediol was 93% in the water layer. The extraction rate of N-hydroxyphthalimide in the organic layer was 75%, based on the amount of N-hydroxyphthalimide in the reaction mixture. The N-hydroxyphthalimide was recovered by concentrating the organic layer to remove the solvent and unreacted 1,3-butadiene.

Example 7

A mixture of toluene (9.21 g, 100 mmol), N-hydroxyphthalimide (1.6 g, 10 mmol), acetylacetonatocobalt(II) Co(AA)$_2$ (0.15 g, 0.5 mmol) and acetic acid (250 ml) was made to react for six hours at 100° C. under an oxygen atmosphere. Toluene was converted into benzoic acid at 95%, the yield being 95%. After removal of the acetic acid by distillation, benzonitrile (400 ml) and water (400 ml) containing sodium hydroxide (3.8 g, 95 mmol) were added to the reaction mixture. The mixture was mixed well by shaking, and then laid still to be separated into two layers, a water layer and an organic layer. The separated organic layer was again added with water (400 ml), mixed well by shaking, and laid still for layer separation. The organic layer, and the water layers which were made acidic using hydrochloric acid were analysed by means of gas chromatography and liquid chromatography. Benzoic acid was extracted into the water layer at a rate of 90% (extracted as sodium benzoate). In the organic layer, the extraction rate of N-hydroxyphthalimide was 85% based on the amount of N-hydroxyphthalimide contained in the reaction mixture.

Example 8

A mixture of 2-methylpyridine (9.3 g, 100 mmol), N-hydroxyphthalimide (1.6 g, 10 mmol), acetylacetonatocobalt(II) Co(AA)₂ (0.15 g, 0.5 mmol) and acetic acid (250 ml) was stirred under an oxygen atmosphere for six hours at 100° C. At a conversion rate of 82%, 2-methylpyridine was converted into 2-pyridinecarboxylic acid (picolinic acid) with a yield of 77%. After removal of acetic acid by distillation, benzonitrile (400 ml) and water (400 ml) were added to the reaction mixture, and mixed completely by shaking. The mixture was left still for layer separation. The separated organic layer was further added with water (400 ml), mixed completely by shaking and then laid still so as to be separated into two layers. The analysis of the organic layer and the water layers by gas chromatography and liquid chromatography indicated that 2-pyridinecarboxylic acid was extracted into the water layer at 85% and that N-hydroxyphthalimide was extracted into the organic layer at 80% based on the amount of N-hydroxyphthalimide.

What is claimed is:

1. A process for separating an oxidation reaction product and an oxidation catalyst from a reaction mixture obtained by oxidation of a substrate selected from the group consisting of an hydrocarbon, an alcohol, an aldehyde, a ketone, an amine, an heterocyclic compound, a thiol and a sulfide in the presence of an imide compound shown by the formula (1) as the oxidation catalyst, which comprises using an aqueous solvent containing at least water and a non-water-soluble solvent separable from said aqueous solvent, thereby distributing the oxidation reaction product by phase separation into a layer of the aqueous solvent and the oxidation catalyst into an immiscible layer of the non-water-soluble solvent,

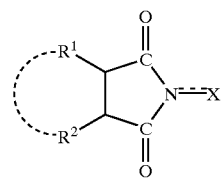

(1)

wherein $R^1$ and $R^2$ independently represent a hydrogen atom, a halogen atom, an alkyl group, an aryl group, a cycloalkyl group, a hydroxyl group, an alkoxy group, a carboxyl group, an alkoxycarbonyl group, or an acyl group, or $R^1$ and $R^2$ may bond together to form a double bond, or an aromatic or non-aromatic ring, and the aromatic or non-aromatic ring formed by $R^1$ and $R^2$ may have 1 or 2 of an imide unit shown by the following formula:

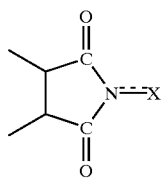

and X indicates an oxygen atom or a hydroxyl group and said aromatic or non-aromatic ring may have substituents $R^3$, $R^4$, $R^5$ and $R^6$ wherein each represents a hydrogen atom, an alkyl group, an hydroxyl group, an alkoxy group, a carboxyl group, an alkoxy carbonyl group, a acyl group, a nitro group, a cyano group, an amino group, or a halogen atom.

2. A separation process as claimed in claim 1, wherein $R^1$ and $R^2$ of the imide compound of the formula (1) bond together to form an aromatic or nonaromatic 5- to 12-membered ring.

3. A separation process under the mild conditions as claimed in claim 1, wherein the imide compound is one of the compounds shown by the following formulas (1a) to (1f)

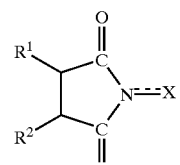

(1a)

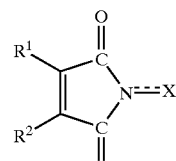

(1b)

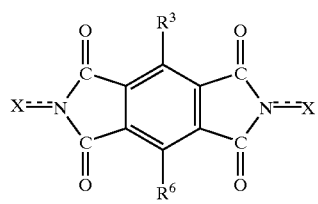

(1c)

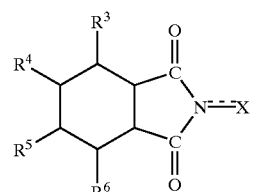

(1d)

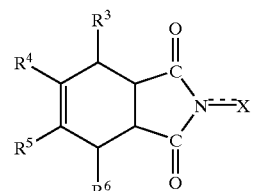

(1e)

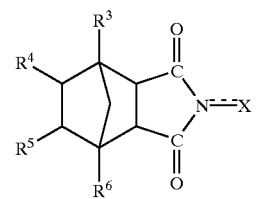

(1f)

wherein each of $R^3$, $R^4$, $R^5$ and $R^6$ represents a hydrogen atom, an alkyl group, a hydroxy group, an alkoxy group, a carboxyl group, an alkoxycarbonyl group, an acyl group, a nitro group, a cyano group, an amino group or a halogen atom; and $R^1$, $R^2$ and X have the same meanings as in claim 1.

4. A separation process as claimed in claim 1, wherein said substrate is a hydrocarbon, an alcohol, an aldehyde, a ketone, an amine or a heterocyclic compound.

5. A separation process as claimed in claim 4, wherein said hydrocarbon is any of (1) a saturated or unsaturated aliphatic hydrocarbon which may have a substituent, (2) a saturated or unsaturated alicyclic hydrocarbon which may have a substituent, (3) a condensed cyclic compound containing a nonaromatic ring, (4) a bridged cyclic hydrocarbon containing a tertiary carbon atom, or (5) a methyl group-containing aromatic hydrocarbon.

6. A separation process as claimed in claim 5, wherein said unsaturated aliphatic hydrocarbon is a conjugated diene or a compound having a carbon-hydrogen bond at a position adjacent to an unsaturated bond.

7. A separation process as claimed in claim 5, wherein said alicyclic hydrocarbon is a 3- to 30-membered cycloalkane which may have a substituent.

8. A separation process as claimed in claim 4, wherein said alcohol is a primary or secondary alcohol.

9. A separation process as claimed in claim 4, wherein said substrate is a compound selected from the group consisting of a cycloalkane, a cycloalkanol, and a cycloalkanone.

10. A separation process as claimed in claim 4, wherein said substrate is a non-water-soluble compound.

11. A separation process as claimed in claim 1 for separating a carboxylic acid and the oxidation catalyst from a reaction mixture containing the carboxylic acid as the reaction product, which process comprises using water and an organic solvent which is incompatible with water, thereby distributing a salt of the carboxylic acid formed with a basic substance into a layer of water and the oxidation catalyst into a layer of the organic solvent.

12. A separation process as claimed in claim 1, wherein said non-water-soluble solvent is at least one species selected from the group consisting of hydrocarbons, alcohols, ketones, esters, nitro compounds and nitriles.

13. A separation process as claimed in claim 12, wherein said non-water-soluble solvent is at least one species selected from the group consisting of (1) aliphatic, alicyclic or aromatic hydrocarbons, (2) halogenated hydrocarbons, (3) aliphatic, alicyclic or aromatic alcohols, (4) aliphatic or alicyclic ketones, (5) aliphatic or aromatic ester compounds, (6) aliphatic or aromatic nitro compounds and (7) aromatic nitriles.

14. A separation process as claimed in claim 1, wherein the proportion of the aqueous solvent containing at least water relative to the non-water-soluble solvent is such that the former/the latter is 0.1/1 to 10/1 (by weight).

15. A separation process as claimed in claim 1, wherein said oxidation reaction product has a boiling point of 0 to 500° C.

16. A separation process as claimed in claim 1, wherein said oxidation reaction product has a boiling point of 150 to 500° C.

17. A separation process as claimed in claim 1, wherein said substrate is a compound selected from the group consisting of an alicyclic hydrocarbon each having a 5- to 20-membered nonaromatic ring, an alcohol corresponding to the hydrocarbon and a ketone corresponding to the hydrocarbon.

18. A separation process as claimed in claim 1, wherein N-hydroxyphthalimide is distributed into the organic layer and the oxidation reaction product or its salt is distributed into the water layer from a reaction mixture by means of water and an organic solvent incompatible with water, said reaction mixture being obtained by oxidizing, in the presence of N-hydroxyphthalimide as the oxidation catalyst, at least one compound selected from the group consisting of 5- to 16-membered alicyclic hydrocarbons, alcohols corresponding to said hydrocarbons and ketones corresponding to said hydrocarbons.

19. A separation process as claimed in claim 1, wherein N-hydroxyphthalimide is distributed into the organic layer and adipic acid or its salt is distributed into the water layer from a reaction mixture by means of water and an organic solvent incompatible with water, said reaction mixture containing adipic acid obtained by oxidizing, in the presence of N-hydroxyphthalimide as the oxidation catalyst, at least one compound selected from the group consisting of cyclohexane, cyclohexanol and cyclohexanone.

20. A process for separating an oxidation reaction product and an oxidation catalyst from a reaction mixture obtained by oxidation of a substrate selected from the group consisting of a hydrocarbon, an alcohol, an aldehyde, a ketone, an amine, an heterocyclic compound, a thiol, and a sulfide in the presence of a N-hydroxyimide or N-oxyimide compound corresponding to a polycarboxylic anhydride as the oxidation catalyst, which comprises using an aqueous solvent containing at least water and non-water-soluble solvent separable from said aqueous solvent, thereby distributing the oxidation reaction product into a layer of the aqueous solvent and the oxidation catalyst into a layer of the non-water-soluble solvent+.

* * * * *